United States Patent

Kajiwara et al.

[11] Patent Number: 5,931,784
[45] Date of Patent: Aug. 3, 1999

[54] ULTRASONIC DIAGNOSTIC APPARATUS

[75] Inventors: Souichi Kajiwara; Shinji Ishihara, both of Nishinomiya, Japan

[73] Assignee: Furuno Electric Co., Ltd., Hyogo-ken, Japan

[21] Appl. No.: 08/945,644

[22] PCT Filed: Mar. 14, 1997

[86] PCT No.: PCT/JP97/00828

§ 371 Date: Feb. 2, 1998

§ 102(e) Date: Feb. 2, 1998

[87] PCT Pub. No.: WO97/34530

PCT Pub. Date: Sep. 25, 1997

[30] Foreign Application Priority Data

Mar. 18, 1996 [JP] Japan ............................. HE18/90345

[51] Int. Cl.$^6$ ...................................................... A61B 8/06
[52] U.S. Cl. ............................ 600/441; 600/443; 128/916
[58] Field of Search ................................. 600/441, 443, 600/445–460; 128/916

[56] References Cited

U.S. PATENT DOCUMENTS

| 4,794,932 | 1/1989 | Baba . |
| 5,105,817 | 4/1992 | Uchibori et al. ..................... 600/454 |
| 5,720,291 | 2/1998 | Schwartz ............................ 128/916 |

FOREIGN PATENT DOCUMENTS

| 62-229192 | 10/1987 | Japan . |
| 3-5173550 | 7/1991 | Japan . |
| 6-178777 | 6/1994 | Japan . |
| 7-59771 | 3/1995 | Japan . |

Primary Examiner—Francis J. Jaworski
Attorney, Agent, or Firm—Birch, Stewart, Kolasch & Birch, LLP

[57] ABSTRACT

The present invention is directed to an ultrasound diagnostic apparatus which can display a superimposed picture of both B-mode and color flow mode images without loosing information of either image. The ultrasound diagnostic apparatus transmits an ultrasonic pulse signal to a specified region of a living body including its moving parts such as a blood flow and displays a status within that region of the living body based on reflected ultrasonic waves which have been received. The apparatus B-mode image display signal acquisition means for acquiring a B-mode image display signal derived from the scanned region, color flow mode image display signal acquisition means for acquiring a color flow mode image display signal which represents information on movements of blood and other moving parts in colors, translucent display processing means which performs a translucent display operation on the B-mode image display signal and the color flow mode image display signal, and display means which displays a synthesized image produced by superimposing a B-mode image and a color flow mode image based on a signal fed from the translucent display processing means.

10 Claims, 9 Drawing Sheets

RGB ORTHOGONAL COLOR COORDINATE SYSTEM

ULTRASONIC DIAGNOSTIC APPARATUS

TECHNICAL FIELD

The present invention relates to an ultrasound diagnostic apparatus which can effectively diagnose a specified region of a living body including its moving parts such as blood flows. More particularly, the invention relates to an ultrasound diagnostic apparatus which enables simultaneous observation of a B-mode picture in which obtained data is displayed in accordance with echo intensities and a color picture in which information on movements of blood, walls of blood vessels and heart muscle, for instance, is displayed in colors.

DESCRIPTION OF THE BACKGROUND ART

One known example of the prior art is an ultrasound diagnostic apparatus which can display a B-mode image representing echo intensities and a color flow mode image depicting directions and velocities of blood flows. This ultrasound diagnostic apparatus was constructed in such a way that it could display only the B-mode image or the color flow mode image of any given area, allowing an operator to specify a desired area in the B-mode image to present the color flow mode image within that area.

SUMMARY OF THE INVENTION

With conventional ultrasound diagnostic apparatuses, no color flow mode image was displayed in an area where B-mode information was displayed, while no B-mode image was displayed in an area where a color flow mode image was displayed. Thus, the conventional apparatuses have been associated with a problem that there was no alternative but to present diagnostic information in only one display mode for any given area, omitting information in the other display mode. One approach to the solution of this problem would be to use a mixed display method in which a B-mode image and a color flow mode image are superimposed. It has however been confirmed that both images are blurred in superimposed presentation according to the mixed display method and become difficult to discriminate.

Accordingly, it is an object of the invention to provide an ultrasound diagnostic apparatus which can display a superimposed picture of both B-mode and color flow mode images without loosing information of either image.

It is another object of the invention to provide an ultrasound diagnostic apparatus which displays a picture by performing a translucent display operation on a B-mode image display signal obtained from B-mode image display signal acquisition means and on a color flow mode image display signal obtained from color now mode image display signal acquisition means.

It is still another object of the invention to provide an ultrasound diagnostic apparatus which displays a picture by performing a translucent display operation on a B-mode image display signal obtained from B-mode image display signal acquisition means and on a power Doppler image display signal obtained from power Doppler image display signal acquisition means.

It is yet another object of the invention to provide an ultrasound diagnostic apparatus which displays a picture by performing a translucent display operation on a B-mode image display signal and on a signal representative of the variance of blood flows.

A first feature of the invention is that an ultrasound diagnostic apparatus which transmits an ultrasonic pulse signal to a specified region of a living body including its moving parts such as a blood flow and displays a status within that region of the living body based on reflected ultrasonic waves which have been received comprises B-mode image display signal acquisition means for acquiring a B-mode image display signal derived from the scanned region, color flow mode image display signal acquisition means for acquiring a color flow mode image display signal which represents information on movements of blood and other moving parts in colors, translucent display processing means which performs a translucent display operation on the B-mode image display signal fed from the B-mode image display signal acquisition means and the color flow mode image display signal fed from the color flow mode image display signal acquisition means, and display means which displays a synthesized image produced by superimposing a B-mode image and a color flow mode image based on a signal fed from the translucent display processing means.

A second feature of the invention is that an ultrasound diagnostic apparatus which transmits an ultrasonic pulse signal to a specified region of a living body including its moving parts such as a blood flow and displays a status within that region of the living body based on reflected ultrasonic waves which have been received comprises B-mode image display signal acquisition means for acquiring a B-mode image display signal derived from the scanned region, power Doppler image display signal acquisition means for acquiring a power Doppler image display signal which represents blood flow intensities in colors, translucent display processing means which performs a translucent display operation on the B-mode image display signal fed from the B-mode image display signal acquisition means and the power Doppler image display signal fed from the power Doppler image display signal acquisition means, and display means which displays a synthesized image produced by superimposing a B-mode image and a power Doppler image based on a signal fed from the translucent display processing means.

A third feature of the invention is that an ultrasound diagnostic apparatus which transmits an ultrasonic pulse signal to a specified region of a living body including its moving parts such as a blood flow and displays a status within that region of the living body based on reflected ultrasonic waves which have been received comprises B-mode image display signal acquisition means for acquiring a B-mode image display signal derived from the scanned region, color flow mode image display signal acquisition means for acquiring a color flow mode image display signal representing information on movements of blood and other moving parts in a plurality of colors, first translucent display processing means which performs a translucent display operation on the B-mode image display signal fed from the B-mode image display signal acquisition means and the color flow mode image display signal fed from the color flow mode image display signal acquisition means, power Doppler image display signal acquisition means for acquiring a power Doppler image display signal which represents blood flow intensities in colors of a single hue, second translucent display processing means which performs a translucent display operation on the B-mode image display signal fed from the B-mode image display signal acquisition means and the power Doppler image display signal fed from the power Doppler image display signal acquisition means, and display means which selectively displays a synthesized image based on a signal fed from the first or second translucent display processing means.

According to claim 1 of the invention, an ultrasound diagnostic apparatus which transmits an ultrasonic pulse signal to a specified region of a living body including its moving parts such as a blood flow and displays a status within that region of the living body based on reflected ultrasonic waves which have been received comprises B-mode image display signal acquisition means for acquiring a B-mode image display signal derived from the region, color flow mode image display signal acquisition means for acquiring a color flow mode image display signal which represents information on movements of blood and other moving parts in colors, translucent display processing means which performs a translucent display operation on the B-mode image display signal fed from the B-mode image display signal acquisition means and the color flow mode image display signal fed from the color flow mode image display signal acquisition means, and display means which displays a synthesized image produced by superimposing a B-mode image and a color flow mode image based on a signal fed from the translucent display processing means. In this aspect of the invention, the B-mode image and color flow mode image are combined by way of the translucent display operation. The synthesized, or superimposed, image can therefore be displayed without blurring, in which the color flow mode image can be observed through the overlapping B-mode image.

According to claim 2 of the invention, the translucent display operation mentioned in claim 1 is accomplished by varying the brightness of each pixel of the color flow mode image in accordance with the brightness of a corresponding pixel of the B-mode image. In this aspect of the invention, the translucent display operation is performed by altering image brightness. Accordingly, the color flow mode image retains its original hue, and this ensures the non-blurring, see-through viewing effect of claim 1.

According to claim 3 of the invention, alteration of image brightness stated in claim 2 is accomplished by multiplying the brightness of each pixel of the color flow mode image by the brightness of a corresponding pixel of the B-mode image. In this aspect of the invention, the image brightness is varied by a simple multiplying process so that the effect of claim 2 can be easily achieved.

According to claim 4 of the invention, alteration of image brightness stated in claim 2 is accomplished by multiplying the brightness of each pixel of the color flow mode image by a coefficient obtained by adding a specific coefficient to a coefficient which is proportional to the brightness of a corresponding pixel of the B-mode image. In this aspect of the invention, multiplying factors are weighted. Accordingly, superimposed portions can be displayed with increased brightness, and this serves to improve the see-through viewing effect of claim 2.

According to claim 5 of the invention, alteration of image brightness stated in claim 2 is accomplished as follows: if the brightness of a pixel of the B-mode image is lower than a specific threshold, image brightness is varied by increasing the brightness of that pixel by a specific amount and multiplying the brightness of a corresponding pixel of the color flow mode image by the increased brightness of the pixel of the B-mode image and, if the brightness of a pixel of the B-mode image is higher than the threshold, image brightness is varied by simply multiplying the brightness of a corresponding pixel of the color flow mode image by the original brightness of the pixel of the B-mode image. In this aspect of the invention, the brightness of each pixel of the B-mode image is altered. It is therefore possible to display blood vessel regions with increased brightness, and this serves to improve the see-through viewing effect of claim 2.

According to claim 6 of the invention, an ultrasound diagnostic apparatus which transmits an ultrasonic pulse signal to a specified region of a living body including its moving parts such as a blood flow and displays a status within that region of the living body based on reflected ultrasonic waves which have been received comprises B-mode image display signal acquisition means for acquiring a B-mode image display signal derived from the region, power Doppler image display signal acquisition means for acquiring a power Doppler image display signal which represents blood flow intensities in colors, translucent display processing means which performs a translucent display operation on the B-mode image display signal fed from the B-mode image display signal acquisition means and the power Doppler image display signal fed from the power Doppler image display signal acquisition means, and display means which displays a synthesized image produced by superimposing a B-mode image and a power Doppler image based on a signal fed from the translucent display processing means. In this aspect of the invention, the B-mode image and color-coded power Doppler image are combined by way of the translucent display operation. The synthesized, or superimposed, image can therefore be displayed without blurring, in which the power Doppler image can be observed through the overlapping B-mode image.

According to claim 7 of the invention, the translucent display operation mentioned in claim 6 is accomplished by varying the brightness of each pixel of the power Doppler image in accordance with the brightness of a corresponding pixel of the B-mode image. In this aspect of the invention, the translucent display operation is performed by altering image brightness. Accordingly, the color flow mode image retains its original hue, and this ensures the non-blurring, see-through viewing effect of claim 6.

According to claim 8 of the invention, alteration of image brightness stated in claim 2 is accomplished by inverting the brightness of each pixel of the B-mode image and multiplying the inverted brightness by the brightness of a corresponding pixel of the B-mode image. In this aspect of the invention, the brightness of the B-mode image is inverted, and this serves to enhance the non-blurring, see-through viewing effect of claim 7.

According to claim 9 of the invention, an ultrasound diagnostic apparatus which transmits an ultrasonic pulse signal to a specified region of a living body including its moving parts such as a blood flow and displays a status within that region of the living body based on reflected ultrasonic waves which have been received comprises B-mode image display signal acquisition means for acquiring a B-mode image display signal derived from the region, color flow mode image display signal acquisition means for acquiring a color flow mode image display signal representing information on movements of blood and other moving parts in a plurality of colors, first translucent display processing means which performs a translucent display operation on the B-mode image display signal fed from the B-mode image display signal acquisition means and the color flow mode image display signal fed from the color flow mode image display signal acquisition means, power Doppler image display signal acquisition means for acquiring a power Doppler image display signal which represents blood flow intensities in colors of a single hue, second translucent display processing means which performs a translucent display operation on the B-mode image display signal fed from the B-mode image display signal acquisition means and the power Doppler image display signal fed from the power Doppler image display signal acquisition means, and display means which selectively displays a synthesized image based on a signal fed from the first or second translucent display processing means. In this aspect of the invention, it is possible to selectively superimpose a color flow mode image or a power Doppler mode image which is shown in colors of the single hue. This allows for a choice of alternative presentations on a single display screen depending on specific needs of diagnosing the living body.

According to claim 10 of the invention, the information on the movements of blood and other moving parts or blood flow intensities mentioned in claims 1, 6 and 9 are displayed in colors of a single hue. In this aspect of the invention, the information on the movements of blood and other moving parts or blood flow intensities can be easily observed as they are displayed in colors of the same hue.

According to claim 11 of the invention, the information on the movements of blood and other moving parts mentioned in claims 1 and 9 is the variance of the blood flow. In this aspect of the invention, the information on the movements of blood and other moving parts is the variance of the blood flow so that the translucent display operation can be applied to the variance of the blood flow as well.

According to claim 12 of the invention, a display apparatus which presents a two-dimensional image by superimposing a first information signal and a second information signal on each other comprises first signal generating means for producing the first information signal, second signal generating means for producing the second information signal which is expressed by a plurality of colors, synthesized image signal acquisition means for producing a synthesized image signal by performing a translucent display operation on the first information signal and the second information signal which is expressed by a plurality of colors, and display means which displays a synthesized image based on the synthesized image signal fed from the synthesized image signal acquisition means. The invention is applicable not only to the ultrasound diagnostic apparatus but also to such display apparatus which presents a two-dimensional image by superimposing a first information signal and a second information signal on each other. In this aspect of the invention, superimposed images can be displayed without blurring, in which the image in the background can be observed through the image in the foreground.

BEST MODES FOR CARRYING OUT THE INVENTION

Figure 1:
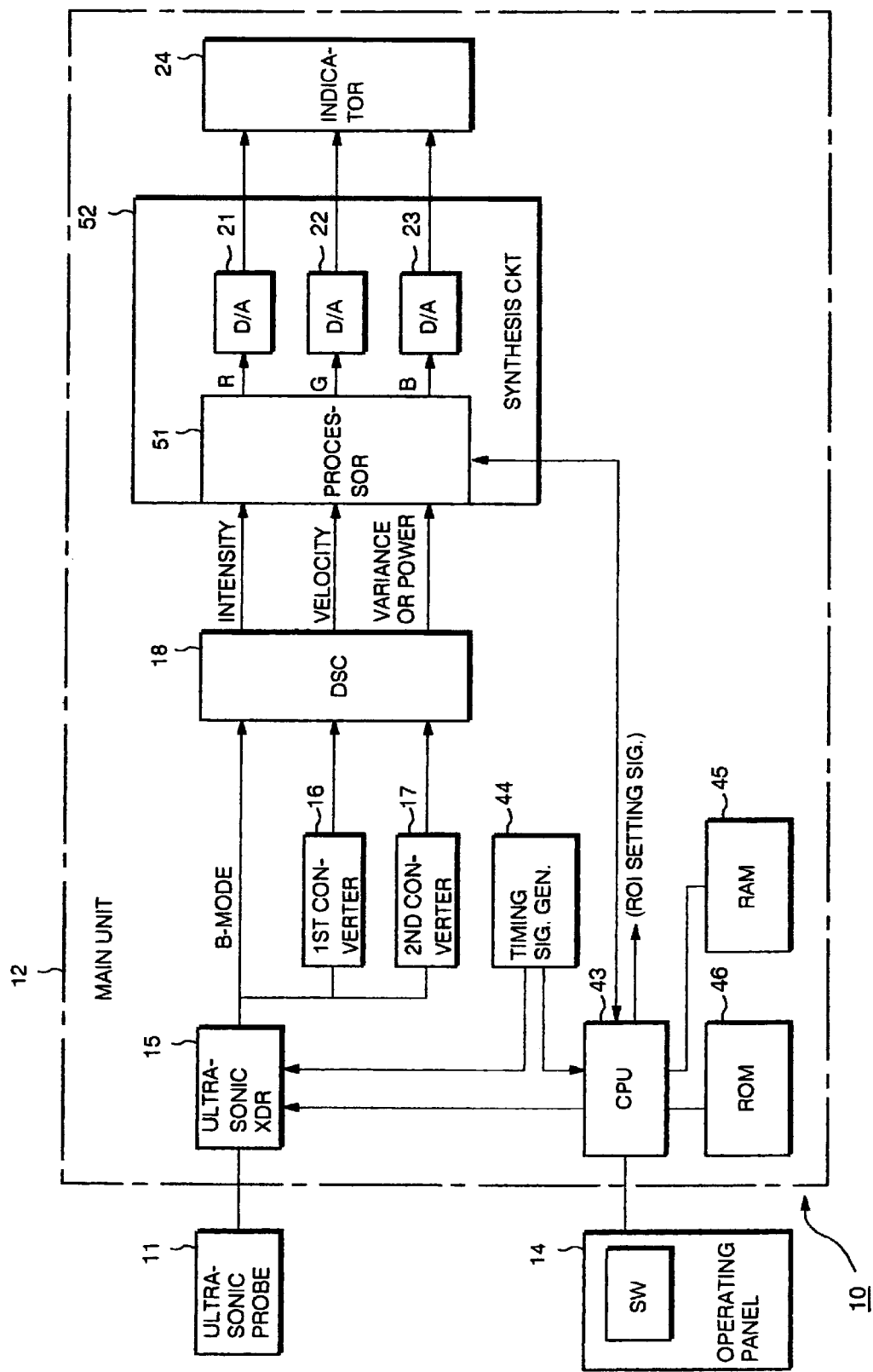
FIG. 1 is a block diagram showing the configuration of an ultrasound diagnostic apparatus according to an embodiment of the invention.

FIG. 1 is a block diagram showing the configuration of an ultrasound diagnostic apparatus.

As shown in FIG. 1, the ultrasound diagnostic apparatus 10 comprises an ultrasonic probe 11 which transmits and receives ultrasonic signals to and from a subject of diagnosis, a main unit 12 which drives the ultrasonic probe 11 and processes a signal received by the ultrasonic probe 11, and an operating panel 14 which is connected to the main unit 12 and makes it possible to transmit information on operator inputs to the whole apparatus.

The main unit 12 can be roughly divided into ultrasonic probe circuitry and operating panel circuitry in accordance with types of signal flows to be handled.

The ultrasonic probe circuitry includes an ultrasonic transceiver 15 which is connected to the ultrasonic probe 11, parallel-connected first and second converters 16, 17 which are connected to an output of the ultrasonic transceiver 15, a digital scan converter (DSC) 18 which is series-connected to outputs of the first converter 16 and second converter 17, a synthesis circuit 52 which is connected to outputs of the DSC 18, and an indicator 24 which is connected to outputs of the synthesis circuit 52.

The operating panel circuitry includes a central processing unit (CPU) 43 to which information on operator inputs is entered, and a timing signal generator 44 which is placed under the control of the CPU 43. The CPU 43 has the ability to deliver a signal for setting a region of interest (ROI) specified by an operator via the operating panel 14 to individual constituent elements concerned with ROI setting operation.

The ultrasonic transceiver 15 forms B-mode image signal acquisition means. The first converter 16 constitutes velocity information display (color flow mode image) signal acquisition means for obtaining information on the velocity of a blood flow, for instance. The information on the blood flow velocity is displayed in colors of two different hues on the indicator 24. The second converter 17 constitutes variance signal acquisition means or power display (power Doppler image) signal acquisition means for obtaining information on the variance or power of the blood flow. Either the variance or power of the blood flow is displayed in colors of a single hue (e.g., orange) on the indicator 24. The synthesis circuit 52, CPU 43 and other circuit elements form synthesized image acquisition means which performs a translucent display operation on relevant signals and generates a synthesized image while the indicator 24 constitutes display means for presenting the synthesized image.

The ultrasonic probe 11 incorporates a transducer formed of a plurality of strip-shaped piezoelectric transducer elements arranged in an array, for instance. The ultrasonic probe 11 receives an output signal from the ultrasonic transceiver 15, transmits an ultrasonic signal into a human body, and delivers a received echo signal back to the ultrasonic transceiver 15. The ultrasonic transceiver 15 is formed of a transmitter and a receiver. The aforementioned piezoelectric transducer elements are individually excited by driving signals fed from the ultrasonic transceiver 15. The direction of a transmitted ultrasonic beam is electronically varied by controlling delay times given to the individual driving signals so that the transmitted beam scans across a region within a sector. A delay time pattern the ultrasonic transceiver 15 applies to the individual driving signals is determined by the CPU 43 using a reference signal fed from the timing signal generator 44 as a time base. Controlled by the CPU 43 in this manner, the ultrasonic transceiver 15 outputs driving voltage signals to the ultrasonic probe 11, the individual driving voltage signals conforming to the delay time pattern determined in accordance with scanning directions (in which the transmitted beam is directed). Upon receiving these driving voltage signals, the individual piezoelectric transducer elements of the ultrasonic probe 11 convert the voltage signals into an ultrasonic signal, which is transmitted toward targets in a human body. The transmitted ultrasonic signal is reflected by body organs including blood vessels back to the ultrasonic probe 1. The individual piezoelectric transducer elements of the ultrasonic probe 11 convert ultrasonic echo signals back into electric signals, and output the electric echo signals to the ultrasonic transceiver 15.

The aforementioned ultrasonic transceiver 15 includes a received signal processing circuit which controls phases of the input echo signals by providing specific time delays in a manner similar to transmission cycles, in order to produce an imaginary receiving beam in a direction in which the transmitted beam was created. The echo signals picked up by the receiving beam are demodulated and output as a B-mode signal to the DSC 18 through a first channel, as a velocity signal to the DSC 18 through a second channel, and as a variance or power signal to the DSC 18 through a third channel.

The DSC 18 performs coordinate transformation, in which data derived from the B-mode signal, velocity signal, and variance or power signal are converted into values for individual pixel locations of a raster scan format of the indicator 24, and the signals thus converted are individually output to the synthesis circuit 52.

The synthesis circuit 52 includes a processor 51, a red (R) component digital-to-analog (D/A) converter 21, a green (G) component D/A converter 22, and a blue (B) component D/A converter 23. The processor 51 is controlled by the CPU 43. A function of the processor 51 is to perform operations using two signals according to an operating flow shown in FIG. 2, for example, and convert signals for the individual pixel locations obtained by the operation into RGB values under the control of the CPU 43. This configuration requires less communications with the CPU 43 and enables high-speed operation of the processor 51.

The operations performed by the processor 51 will be described later with reference to drawings including flowcharts.

Comprising a phase detector, a filter circuit and a frequency analyzer, for example, the first converter 16 is for converting the output (B-mode signal) of the ultrasonic transceiver 15 into a velocity signal for color flow mapping (CFM). A circuit configuration for converting the B-mode signal into the velocity signal for color flow mapping (CFM) is known in the prior art.

The phase detector includes a mixer and a low-pass filter. The echo signals reflected by moving parts such as blood flows are shifted in frequency (Doppler shift) due to the Doppler effect. The phase detector performs phase detection to discriminate Doppler frequencies and outputs only low-frequency Doppler signals to the filter circuit.

The filter circuit removes unwanted Doppler signal components and efficiently detects Doppler signals produced by that part of heart muscle which exists in the direction of the ultrasonic beam. To obtain blood flow information, the filter circuit functions as a high-pass filter through which a mixture of Doppler signals produced by the blood flows, heart wall and valve motion in order to remove the unwanted Doppler signal components resulting from other moving parts than blood flows.

The Doppler signals passed through the filter circuit are output to the frequency analyzer in a succeeding stage. The frequency analyzer analyzes blood flow signals (Doppler frequency signals) by a frequency analysis technique based on a fast Fourier transform (FFT) or autocorrelation method and computes average velocities and maximum velocities within observation time (time window) in individual sample volumes. More particularly, the frequency analyzer computes on a real-time basis an average Doppler frequency (which represents the average moving velocity of a target object) and a variance value (which represents the degree of turbulence of Doppler spectrum) at each raster scan pixel location by using the FFT or autocorrelation method, as well as a maximum value of Doppler frequency (which represents the maximum moving velocity of the target object) by using the FFT method. Results of such Doppler frequency analysis are output as color Doppler information.

As previously mentioned, the velocity of each moving object directly detected by an ultrasonic Doppler method is a velocity component in the direction of the ultrasonic beam. The velocity to be actually obtained is an absolute velocity V. An absolute velocity vector can be obtained by using various estimation methods. These include (i) a method in which ultrasonic beams are emitted to a target location of a moving object in two directions at different incident angles from different aperture positions and an absolute velocity vector is estimated based on Doppler shift frequencies obtained by the individually emitted beams; and (ii) a method in which ultrasonic beams are emitted in slightly different two directions from a common aperture and a velocity component (tangential component) in a direction perpendicular to the beams is obtained from resultant Doppler shift frequencies (radial component) to estimate an absolute velocity vector.

The indicator 24 is comprised of a color cathode ray tube (CRT). Now, color display methods for displaying blood flow information is briefly described. There are three basic color display methods: (i) a display of magnitudes (absolute values) of velocity; (ii) a display of moving directions and magnitudes of velocity; and (iii) a display of moving directions. Display method (i) includes two alternative ways of presentation: (a) different magnitudes of velocity are represented by variations in brilliance of a single hue; or (b) different magnitudes of velocity are represented by different hues. One practical form of display method (ii) is to present different moving directions by different hues and different magnitudes of velocity by variations in brilliance. In this approach, practicable methods of representation with respect to moving directions are limited in accordance with the type of velocity information obtained. A conventionally known technique is to represent a motion of an approaching object in red and a motion of a receding object in blue. This technique is used in an embodiment of the invention. Thus, a blood flow approaching the ultrasonic probe 11 is shown in red while a blood flow moving away from the ultrasonic probe 11 is shown in blue. In addition, the blood flows are shown in brighter red or blue (increased brilliance) as the absolute value of a flow velocity increases.

The second converter 17 is for converting the output (B-mode signal) of the ultrasonic transceiver 15 into a variance or power signal representing the variance or power of blood flow velocities. Like the first converter 16, the second converter 17 comprises a wall filter circuit and a frequency analyzer, for example. Using signals I' and Q' output from the wall filter circuit, the frequency analyzer (autocorrelator) calculates power (I'$^2$+Q'$^2$) and outputs it to the synthesis circuit 52. The power (I'$^2$+Q'$^2$) is converted into color display data in the synthesis circuit 52 for presentation in colors of a single hue (e.g., orange). A circuit configuration for converting the B-mode signal into the blood flow velocity variance or power signal is known in the prior art.

Figure 2:
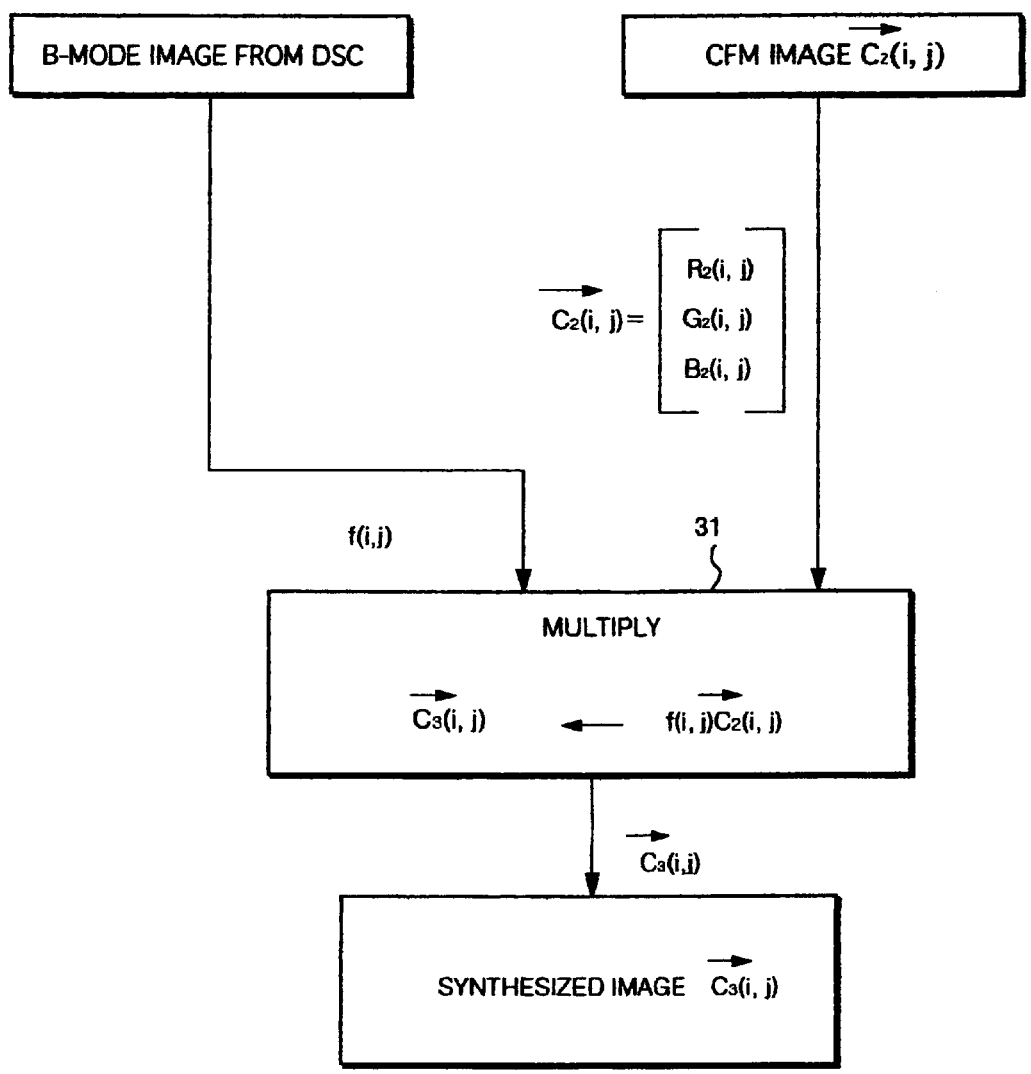
FIG. 2 is a flowchart showing a sequence of operations performed by a synthesis circuit of the embodiment of the invention.

Referring now to FIG. 2, a sequence of operations performed by the processor 51 in producing a translucent display of a color flow mode image (color Doppler plane section image) or a B-mode image is described. A color flow mode image signal vector $C_2(i, j)$ supplied from the first converter 16 to the DSC 18 is multiplied by a B-mode signal f(i, j) fed from the DSC 18 in an arithmetic unit 31 provided within the processor 51 to obtain a synthesized image vector $C_3(i, j)$. The synthesized image vector $C_3(i, j)$ thus produced is individually supplied to the R component D/A converter 21, G component D/A converter 22, and B component D/A converter 23.

A practical example of such translucent display operation is now described below. If a B-mode signal value corresponds to halftone gray, the output f(i, j) becomes 0.51. On the other hand, if a color flow mode image has a value corresponding to blue, the color flow mode image signal vector $C_2$(153, 126) is expressed as follows:

$$\vec{C_2}(153, 126) = \begin{pmatrix} 0 \\ 0 \\ 255 \end{pmatrix}$$

A color vector $C_3$(153, 126) of a synthesized image obtained by superimposition using a translucent display method is expressed as follows:

$$\vec{C_3}(153, 126) = f(153, 126)\vec{C_2}(153, 126)$$
$$= 0.51\begin{pmatrix} 0 \\ 0 \\ 255 \end{pmatrix} = \begin{pmatrix} 0 \\ 0 \\ 130 \end{pmatrix}$$

Details of the aforementioned operations are described with reference to a color coordinate system shown in FIG. 3. In the above example, the output f(i, j) is 0.51 and the value of the B-mode image signal can be expressed by a vector $C_1$(153, 126), which is directed to point ① located on a diagonal joining two points corresponding to black and white in FIG. 3. On the other hand, the color flow mode image signal vector $C_2$(153, 126) having the value corresponding to blue is directed to point ② corresponding to blue. The synthesized image color vector $C_3$(153, 126) is then directed to point ③ which is located between the points corresponding to black and blue. This means that the color flow mode image signal vector $C_2$(153, 126) retains the same hue although its luminosity decreases. More particularly, the luminosity of the color flow mode image signal vector $C_2$(153, 126) varies in accordance with the luminosity of the B-mode image vector $C_1$(153, 126) which lies in the foreground so that the operator can see the color flow mode image through the B-mode image.

If the images are simply superimposed by the mixed display method without using the translucent display method, an image obtained at a mixture ratio of 50:50 would be expressed by the following equation:

$$\vec{C_3}(153, 126) = (1 - 0.5)\vec{C_1}(153, 126) + 0.5\vec{C_2}(153, 126)$$
$$= 0.5\begin{pmatrix} 130 \\ 130 \\ 130 \end{pmatrix} + 0.5\begin{pmatrix} 0 \\ 0 \\ 255 \end{pmatrix} = \begin{bmatrix} 65 \\ 65 \\ 182 \end{bmatrix}$$

Figure 3:
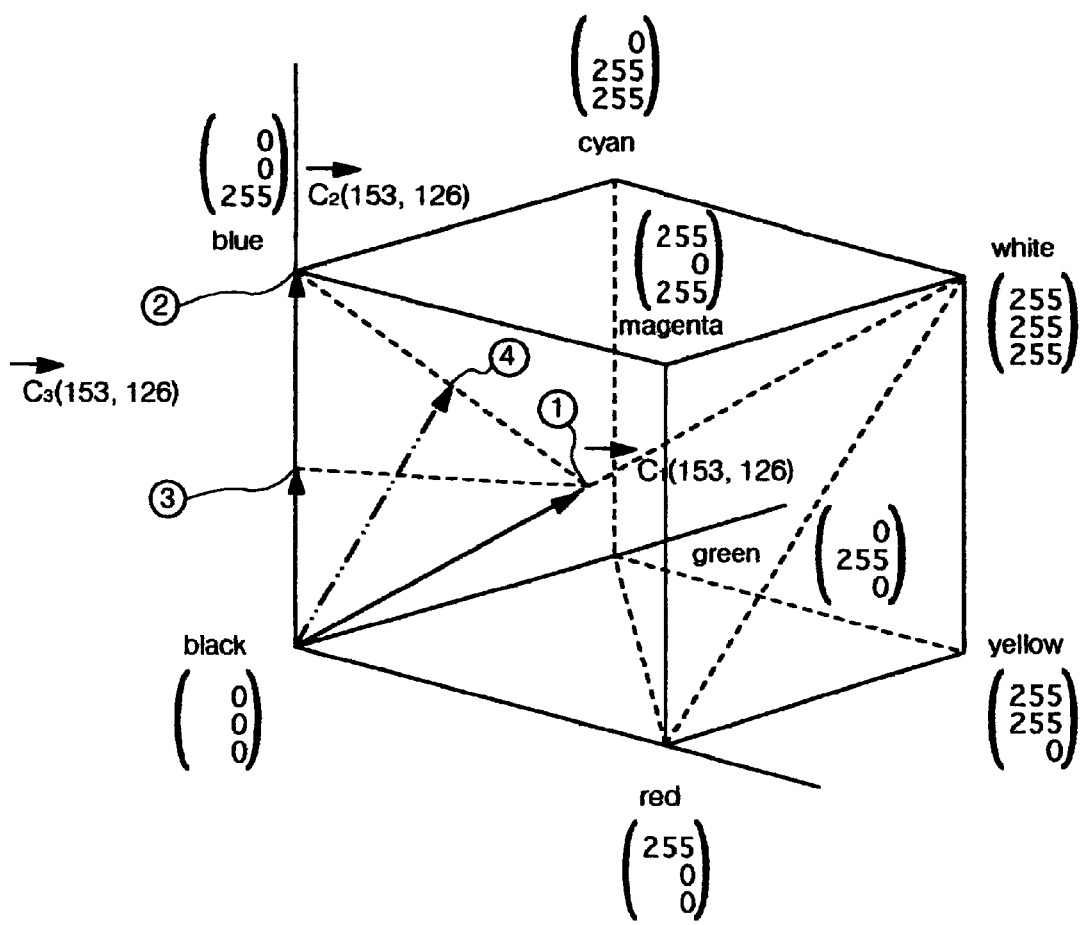
FIG. 3 is a diagram illustrating a manner of color synthesis performed by the synthesis circuit of the embodiment of the invention.

The superimposed image obtained by the mixed display method, as expressed by the above equation, is located at point ④ in the color coordinate system of FIG. 3. This image is blurred as it exists inside a solid body. The foregoing discussion with reference to FIG. 3 has described how velocities of a blood flow moving away from the ultrasonic probe 11 are displayed in blue by the translucent display method. Velocities of a blood flow approaching the ultrasonic probe 11 are displayed in red by the translucent display method in a similar way, in which the horizontal axis (red) is used instead of the vertical axis (blue).

Figure 4:
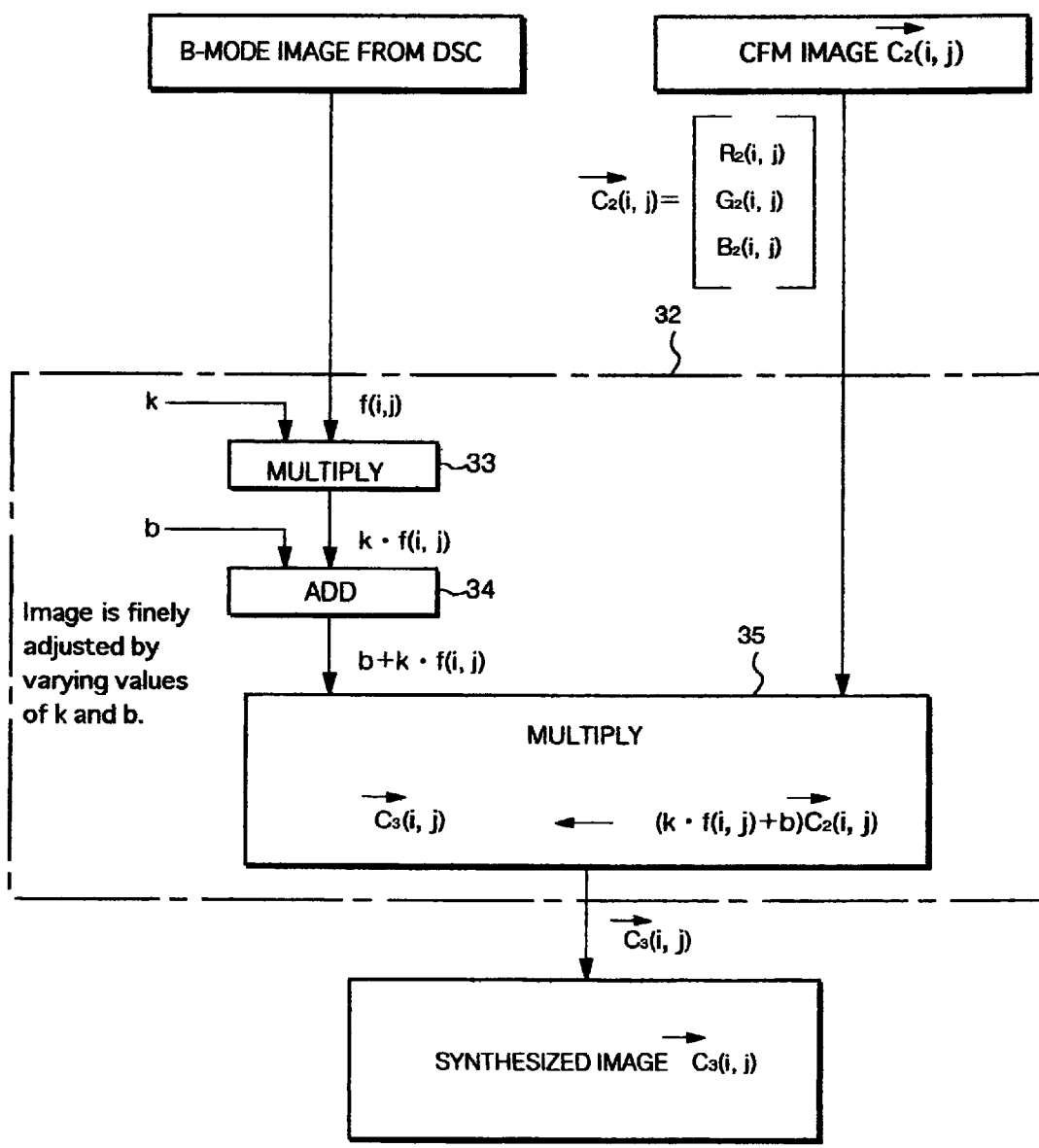
FIG. 4 is a flowchart showing another sequence of operations performed by the synthesis circuit of the embodiment of the invention.

FIG. 4 shows a sequence of operations performed by the processor 51 according to a preferred translucent display method. The sequence differs from that of FIG. 2 in operations of an arithmetic unit 32 which is contained in the processor 51. The B-mode signal f(i, j) fed from the DSC 18 is multiplied by a coefficient k in a multiplier 33 to obtain k·f(i, j), to which a coefficient b is added by an adder 34 to obtain b+k·f(i, j). Next, a multiplier 35 multiplies b+k·f(i, j) by a color flow mode image signal vector $C_2(i, j)$ to obtain the following:

$$\vec{C_3}(i, j) = (b + k \cdot f(i, j)) \times \vec{C_2}(i, j)$$

The coefficients k and b are so determined that each dark portion of an image becomes brighter. This makes it possible to increase the brightness of those portions which are overlapped by the translucent display method and provide easier viewing of a translucent display. It is to be noted, however, that too large values of the coefficients k and b produce an white image, causing a change in hues of some pixels. The coefficients k and b should therefore be set to proper values to avoid such inconvenience.

Figure 5:
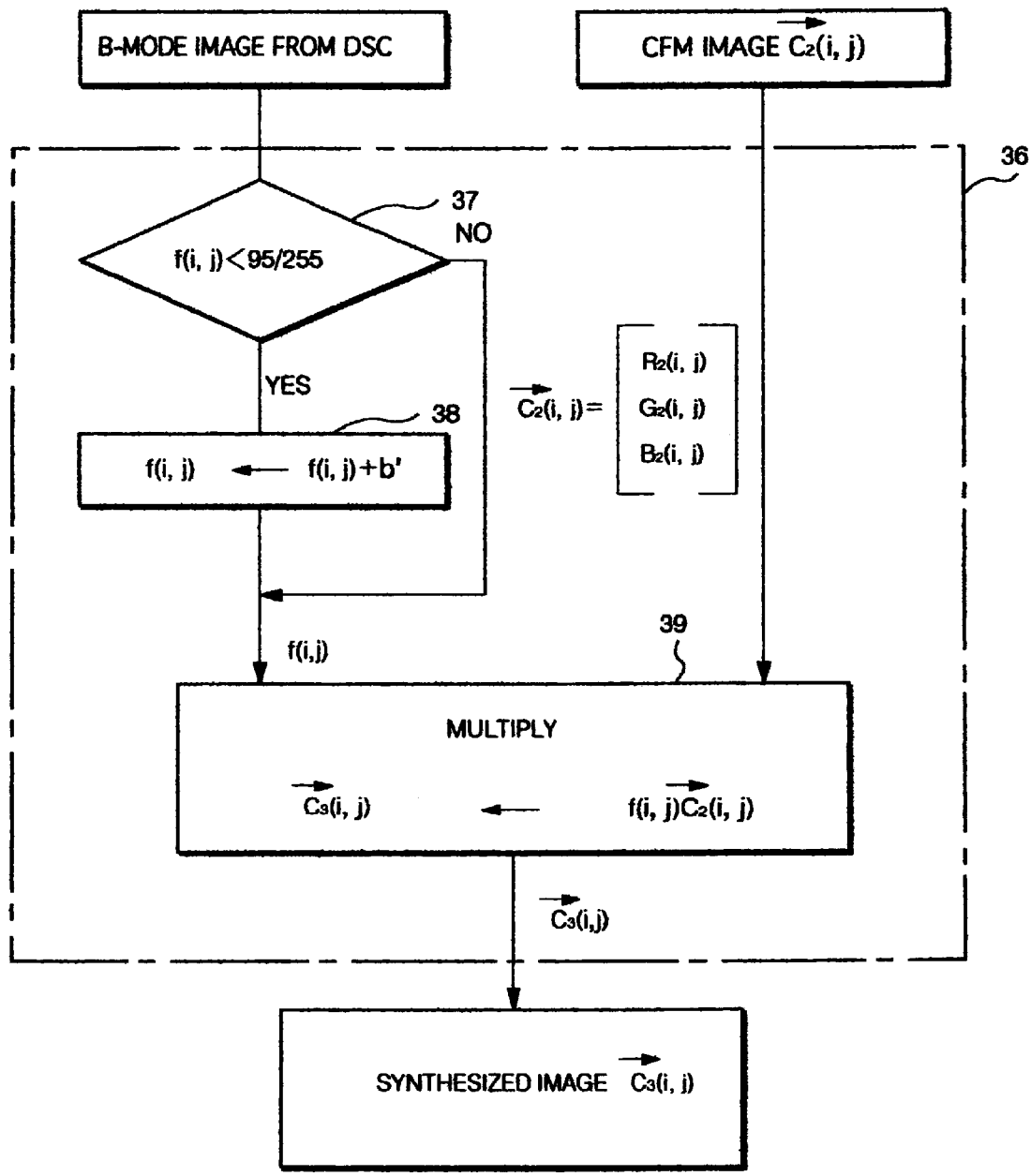
FIG. 5 is a flowchart showing still another sequence of operations performed by the synthesis circuit of the embodiment of the invention.

FIG. 5 shows a sequence of operations performed by the processor 51 according to another preferred translucent display method. The sequence differs from that of FIG. 2 in operations of an arithmetic unit 36 which is contained in the processor 51. More specifically, the sequence of FIG. 5 includes steps 37 and 38 which are executed prior to an operation performed by a multiplier 39. Step 37 compares f(i, j) with a specific threshold (e.g., 95/255). If the value of f(i, j) of a particular pixel is smaller than the threshold, that is, the pixel is darker than a threshold level, a predefined parameter b' is added to f(i, j) in step 38 and the sum is substituted for f(i, j) as shown in FIG. 5. If the value of f(i, j) is larger than the threshold in step 37, that is, the pixel is brighter than the threshold level, step 38 is skipped and the value of f(i, j) is left unchanged. Consequently, blood vessel regions are displayed with increased brightness. Darker pixels are produced if the coefficient b' added in step 38 is small, whereas brighter pixels are produced if the coefficient b' is large. Although this translucent display method makes the blood vessel regions easier to recognize, too high a value of the coefficient b' makes it somewhat difficult to find out their locations. The coefficient b' should therefore be set to a proper value to avoid such inconvenience.

Figure 6:
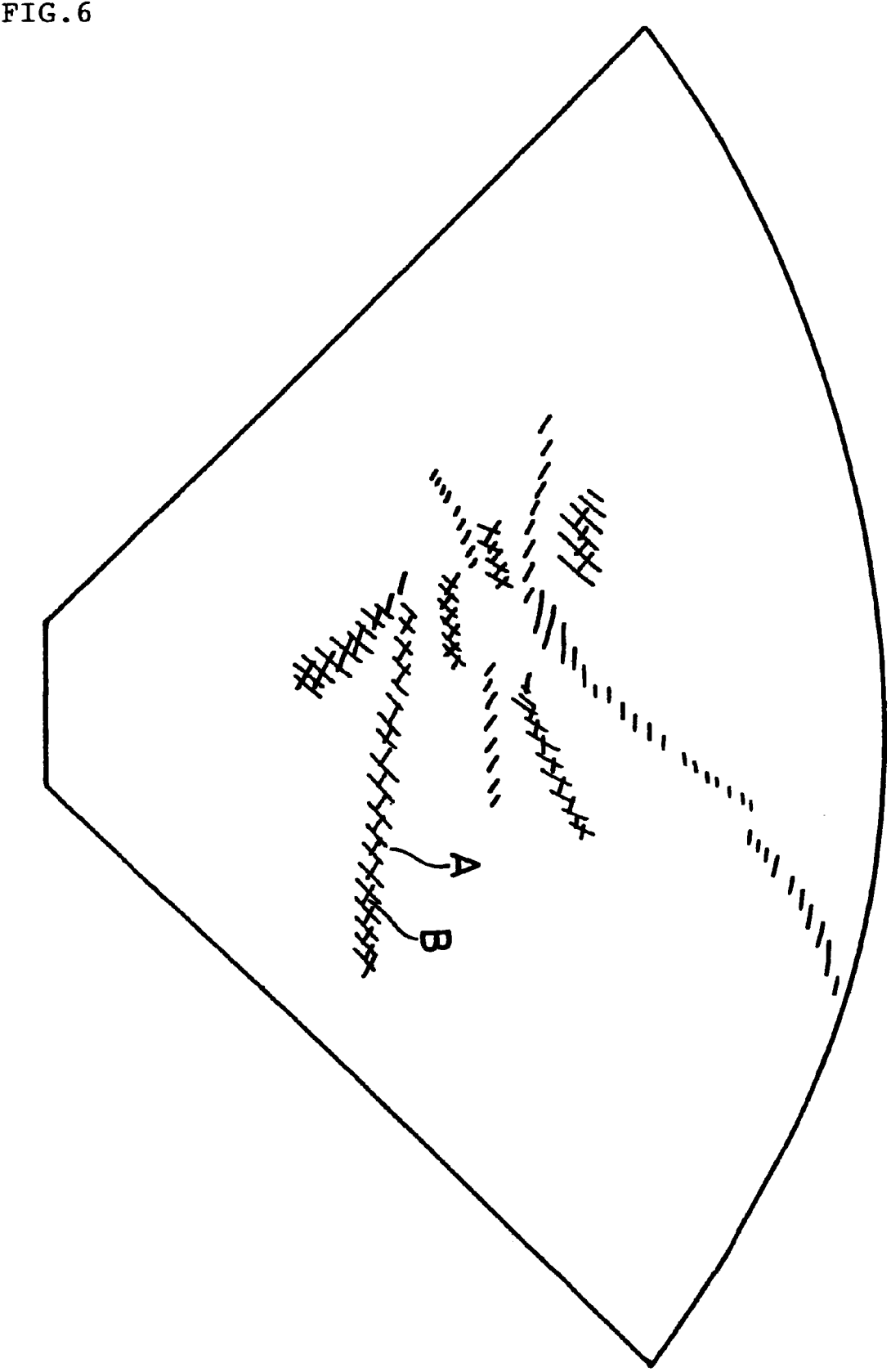
FIG. 6 is a diagram showing an example of presentation on an indicator according to the embodiment of the invention.

As a result, the indicator 24 presents a plane section image like an example shown in FIG. 6, which is produced by superimposing a B-mode plane section image of a living body part (narrow portions in black-and-white gradation as indicated by A) and a color flow mode image representing color-coded blood flow velocities in accordance with a color scale (wider portions in colors of two hues, or red and blue, as indicated by B) by one of the aforementioned translucent display methods.

Figure 7:
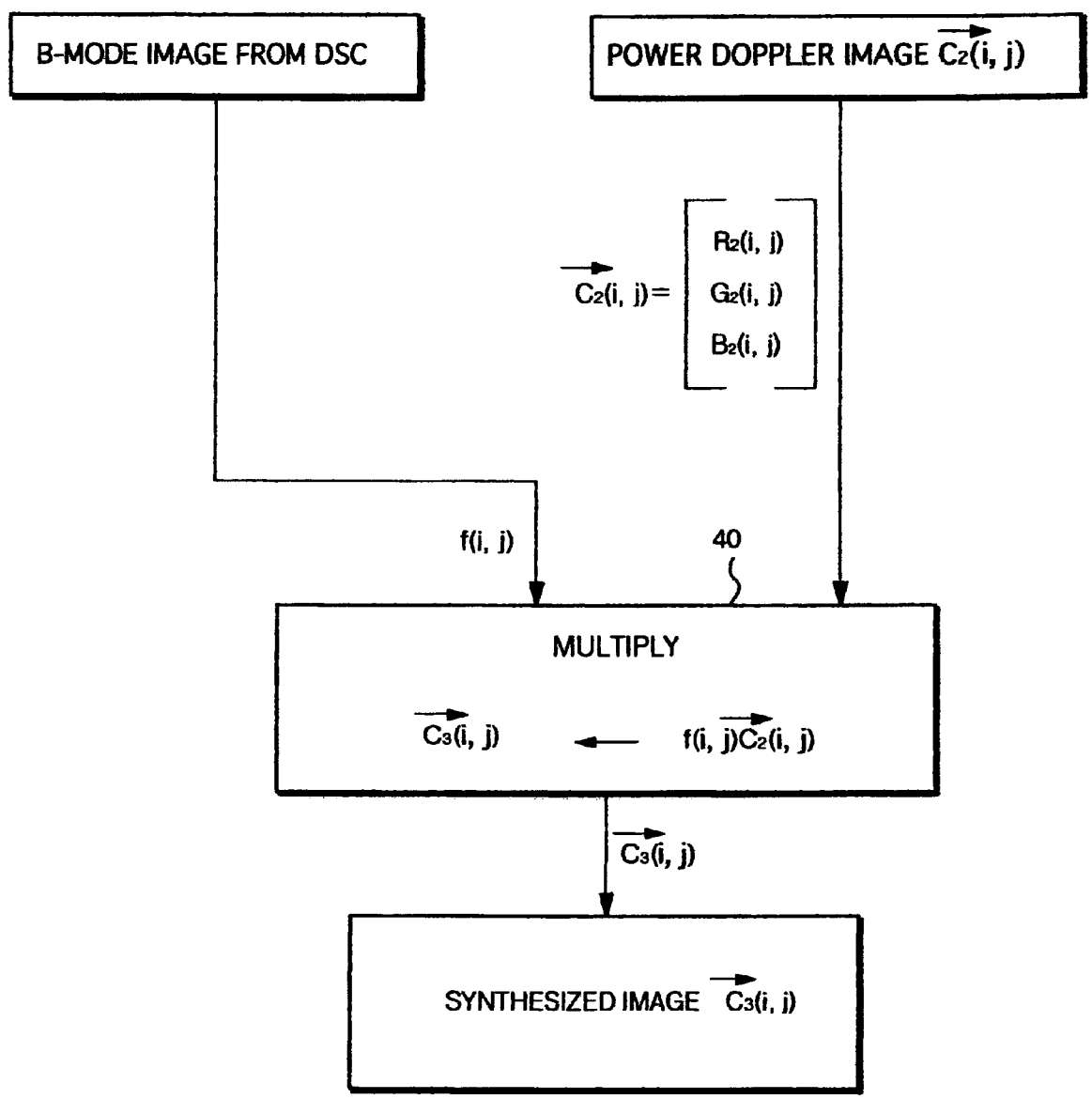
FIG. 7 is a flowchart showing another sequence of operations performed by the synthesis circuit of the embodiment of the invention.

FIG. 7 shows a sequence of operations performed by the processor 51 for power Doppler image presentation. The sequence differs from that of FIG. 2 in that a power Doppler image is superimposed on a B-mode image by a translucent display method and this is performed by use of a multiplier 40 in manner similar to the sequence of FIG. 2. Since the power Doppler image is displayed in colors of a single hue, the power (intensity) ($I'^2+Q'^2$) of Doppler frequency shifts is represented as an easy-to-recognize synthetically generated image.

Figure 8:
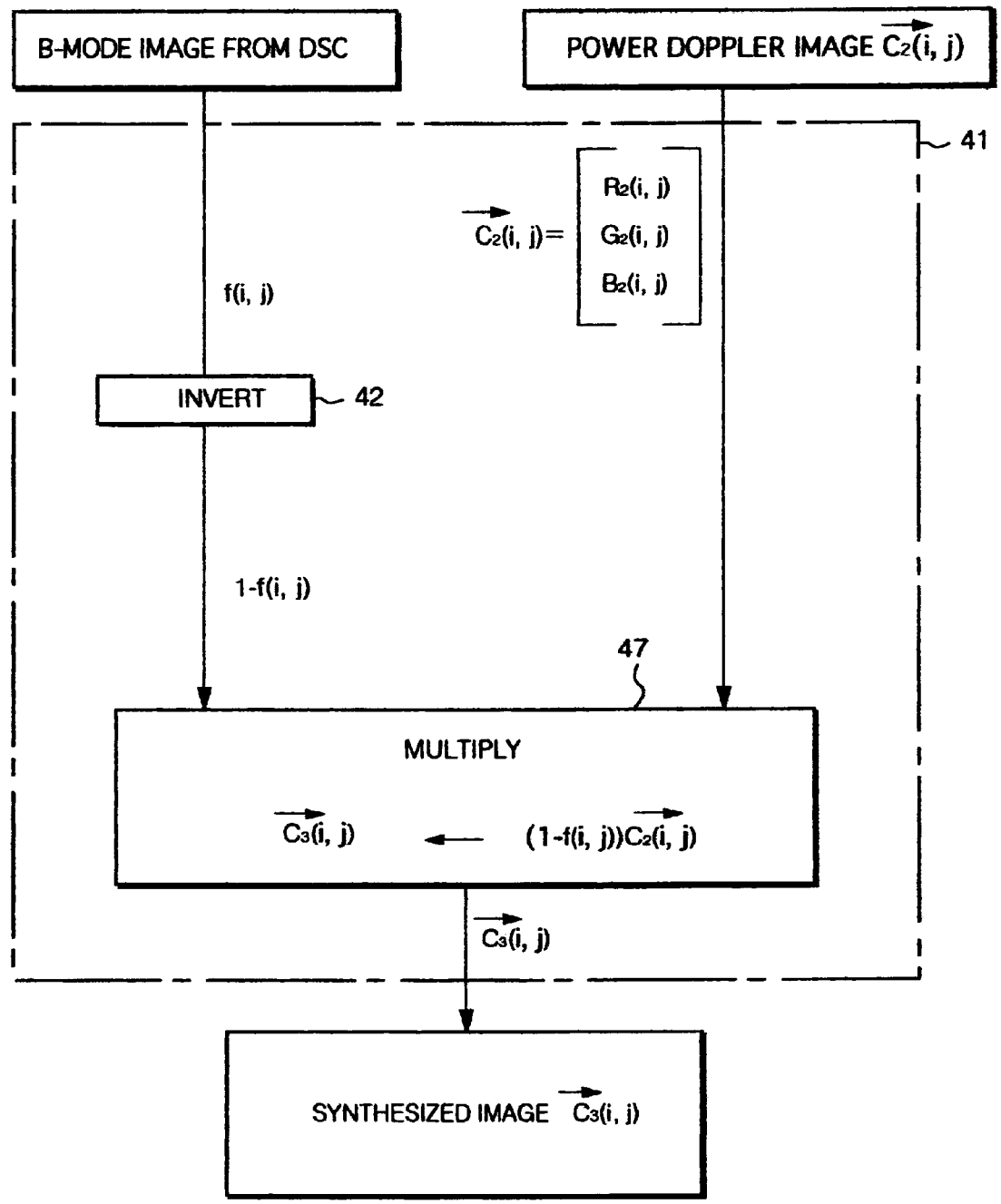
FIG. 8 is a flowchart showing yet another sequence of operations performed by the synthesis circuit of the embodiment of the invention.

FIG. 8 shows a sequence of operations performed by the processor 51 for power Doppler image presentation. The arrangement of FIG. 8 differs from that of FIG. 7 in that a processor 41 includes a reversing circuit 42 preceding a multiplier 43. As the reversing circuit 42 inverts black portions of a B-mode image into white, and vice versa, it becomes easier to recognize overlapped portions. The operator should however get accustomed to observing an inverted monochrome presentation of each B-mode image.

Figure 9:
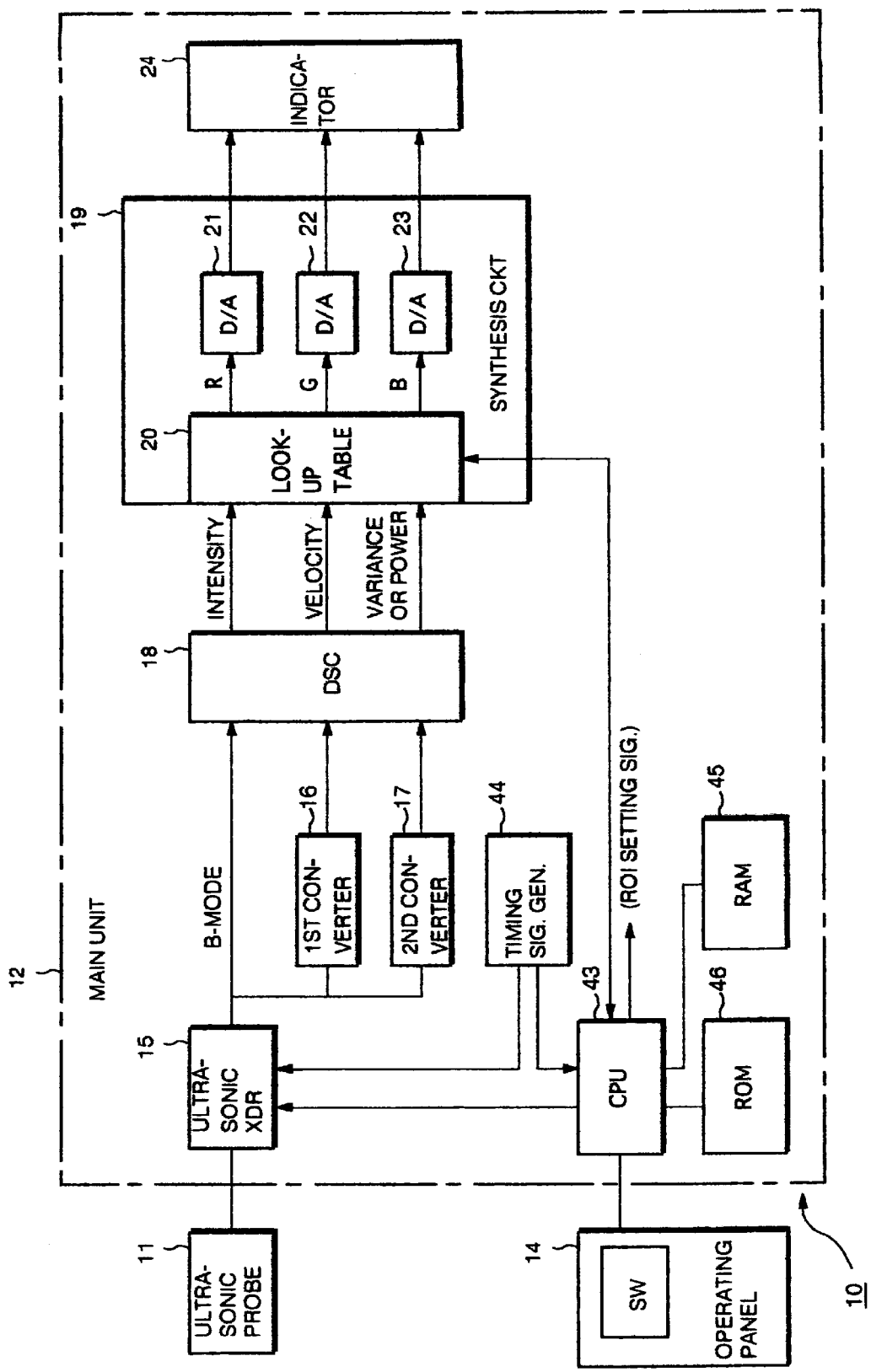
FIG. 9 is a block diagram showing the configuration of an ultrasound diagnostic apparatus according to another embodiment of the invention.

FIG. 9 is a block diagram showing the configuration of an ultrasound diagnostic apparatus according to another embodiment of the invention. The configuration of FIG. 9 differs from the configuration of FIG. 1 in that the former comprises a synthesis circuit 19 in which a look-up table 20 is provided instead of the processor 51 of FIG. 1. The CPU 43 of FIG. 9 performs operations using two signals corresponding to the B-mode signal $f(i, j)$ and color flow mode image signal vector $C_2(i, j)$ according to the operating flow shown in FIG. 2, for example, and stores data obtained by the operations in a random access memory (RAM) 45. More particularly, the CPU 43 performs the operations using various combinations of values of the two signals corresponding to multiple pairs of values of the B-mode signal $f(i, j)$ and color flow mode image signal vector $C_2(i, j)$, the values being chosen from their specified ranges, and synthesized image vectors $C_3(i, j)$ obtained by the operations are stored in the RAM 45. The CPU 43 reads specific signals out of the RAM 45 and writes these signals into the look-up table 20 in response to a control signal entered from the operating panel 14. In an alternative form of the embodiment, the look-up table 20 may be formed of a memory device readily storing synthesized image vectors $C_3(i, j)$ which correspond to various combinations of values of the two signals corresponding to multiple pairs of values of the B-mode signal $f(i, j)$ and color flow mode image signal vector $C_2(i, j)$, the values being chosen from their specified ranges.

When a combination of values of the B-mode signal $f(i, j)$ and color flow mode image signal vector $C_2(i, j)$ has been supplied from the DSC 18, for instance, the look-up table 20 reads out previously stored data (i.e., synthesized image vector $C_3(i, j)$) corresponding to that combination of signals and delivers the data to the red (R) component D/A converter 21, green (G) component D/A converter 22 and blue (B) component D/A converter 23.

A sequence of operations performed in the embodiment of FIG. 9 in producing a translucent display of a color flow mode image (color Doppler plane section image) is now described with reference to the operating flow of FIG. 2. The color flow mode image signal vector $C_2(i, j)$ fed from the first converter 16 to the DSC 18 and the B-mode signal $f(i, j)$ fed from the DSC 18 are supplied to the look-up table 20 in the synthesis circuit 19.

When a combination of values of the B-mode signal $f(i, j)$ and color flow mode image signal vector $C_2(i, j)$ has been supplied, the look-up table 20 reads out previously computed and stored synthesized image vector $C_3(i, j)$ corresponding to that combination of signals and delivers it to the R component D/A converter 21, G component D/A converter 22 and B component D/A converter 23.

A sequence of operations performed in the embodiment of FIG. 9 in producing a translucent display is now described with reference to the operating flow of FIG. 4.

The CPU 43 of FIG. 9 performs operations using two signals corresponding to the B-mode signal $f(i, j)$ and color flow mode image signal vector $C_2(i, j)$ according to the operating flow shown in FIG. 4 and stores data obtained by the operations in the RAM 45.

The signal corresponding to the B-mode signal $f(i, j)$ fed from the DSC 18 is multiplied by a coefficient k in step 33 to obtain $k \cdot f(i, j)$, to which a coefficient b is added by an adder 34 to obtain $b+k \cdot f(i, j)$. Next, the signal corresponding to the color flow mode image signal vector $C_2(i, j)$ is multiplied in step 35 to obtain the following:

$$C_3(i, j) = (b+k \cdot f(i, j)) \times C_2(i, j)$$

The coefficients k and b are so determined that each dark portion of an image becomes brighter. This makes it possible to increase the brightness of those portions which are overlapped by the translucent display method and provide easier viewing of a translucent display. It is to be noted, however, that too large values of the coefficients k and b produce an white image, causing a change in hues of some pixels. The coefficients k and b should therefore be set to proper values to avoid such inconvenience.

When a combination of values of the B-mode signal $f(i, j)$ and color flow mode image signal vector $C_2(i, j)$ has been supplied from the DSC 18, for instance, the look-up table 20 reads out previously computed and stored synthesized image vector $C_3(i, j)$ corresponding to that combination of signals and delivers it to the R component D/A converter 21, G component D/A converter 22 and B component D/A converter 23.

A sequence of operations performed in the embodiment of FIG. 9 in producing a translucent display is now described with reference to the operating flow of FIG. 5.

The CPU 43 of FIG. 9 performs operations using two signals corresponding to the B-mode signal $f(i, j)$ and color flow mode image signal vector $C_2(i, j)$ according to the operating flow shown in FIG. 5 and stores data obtained by the operations in the RAM 45.

The sequence of FIG. 5 differs from that of FIG. 2 in that portion of the operating flow which is indicated by the numeral 36. More specifically, the sequence of FIG. 5 includes steps 37 and 38 which are executed prior to step 39. Step 37 compares $f(i, j)$ with a specific threshold (e.g., 95/255). If the value of $f(i, j)$ of a particular pixel is smaller than the threshold, that is, the pixel is darker than a threshold level, a predefined parameter b' is added to $f(i, j)$ in step 38 and the sum is substituted for $f(i, j)$ as shown in FIG. 5. If the value of $f(i, j)$ is larger than the threshold in step 37, that is, the pixel is brighter than the threshold level, step 38 is skipped and the value of $f(i, j)$ is left unchanged. Consequently, blood vessel regions are displayed with increased brightness. Darker pixels are produced if the coefficient b' added in step 38 is small, whereas brighter pixels are produced if the coefficient b' is large. Although this translucent display method makes the blood vessel regions easier to recognize, too high a value of the coefficient b' makes it somewhat difficult to find out their locations. The coefficient b' should therefore be set to a proper value to avoid such inconvenience.

When a combination of values of the B-mode signal f(i, j) and color flow mode image signal vector $C_2(i, j)$ has been supplied from the DSC 18, for instance, the look-up table 20 reads out previously computed and stored synthesized image vector $C_2(i, j)$ corresponding to that combination of signals and delivers it to the R component D/A converter 21, G component D/A converter 22 and B component D/A converter 23.

A sequence of operations performed in the embodiment of FIG. 9 in producing a translucent display of a power Doppler image is now described with reference to the operating flow of FIG. 7.

The CPU 43 of FIG. 9 performs operations using two signals corresponding to the B-mode signal f(i, j) and power Doppler image signal vector $C_2(i, j)$ according to the operating flow shown in FIG. 7 and stores data obtained by the operations in the RAM 45.

FIG. 7 shows a sequence of operations performed by the CPU 43 for power Doppler image presentation. The sequence differs from that of FIG. 2 in that a power Doppler image is superimposed on a B-mode image by a translucent display method and this is performed by way of step 40 which is similar to step 31 of FIG. 2. Since the power Doppler image is displayed in colors of a single hue, the power (intensity) $(I'^2+Q'^2)$ of Doppler frequency shifts is represented as an easy-to-recognize synthetically generated image.

When a combination of values of the B-mode signal f(i, j) and power Doppler image signal vector $C_2(i, j)$ has been supplied from the DSC 18, for instance, the look-up table 20 reads out previously computed and stored synthesized image vector $C_3(i, j)$ corresponding to that combination of signals and delivers it to the R component D/A converter 21, G component D/A converter 22 and B component D/A converter 23.

A translucent display of a power Doppler image can be produced by the embodiment of FIG. 9 according to the operating flow of FIG. 8 in a manner similar to the operating flow of FIG. 7.

Although the foregoing discussion of the embodiments of the invention has dealt with the methods of translucent display in the ultrasound diagnostic apparatus, the translucent display methods are generally applicable to any display apparatus which presents a two-dimensional image by superimposing a first information signal and a second information signal on each other. In such generalized applications, the B-mode image signal corresponds to the first information signal while the B-mode image signal acquisition means corresponds to first signal generating means. Similarly, the color flow mode image signal or power Doppler image signal corresponds to the second information signal while color flow mode image signal acquisition means or power Doppler image signal acquisition means corresponds to the second signal generating means.

We claim:

1. An ultrasound diagnostic apparatus which transmits an ultrasonic pulse signal to a specified region of a living body including its moving parts such as blood flow and displays a status within said region of the living body based on reflected ultrasonic waves which have been received, said ultrasound diagnostic apparatus comprising:

B-mode image display signal acquisition means for acquiring a B-mode image display signal derived from said region;

color flow mode image display signal acquisition means for acquiring a color flow mode image display signal which represents information on movements of blood and other moving parts in colors;

translucent display processing means which performs a translucent display operation on the B-mode image display signal fed from the B-mode image display signal acquisition means and the color flow mode image display signal fed from the color flow mode by image display signal acquisition means by varying the brightness of each pixel of the color flow mode image in accordance with the brightness of a corresponding pixel of the B-mode image; and display means displaying a synthesized image produced by superimposing a B-mode image and a color flow mode image based on a signal fed from the translucent display processing means.

2. An ultrasound diagnostic apparatus according to claim 1 wherein image brightness is varied by multiplying the brightness of each pixel of the color flow mode image by the brightness of a corresponding pixel of the B-mode image.

3. An ultrasound diagnostic apparatus according to claim 1 wherein image brightness is varied by multiplying the brightness of each pixel of the color flow mode image by a coefficient obtained by adding a specific coefficient to a coefficient which is proportional to the brightness of a corresponding pixel of the B-mode image.

4. An ultrasound diagnostic apparatus according to claim 1 wherein, if the brightness of a pixel of the B-mode image is lower than a specific threshold, image brightness is varied by increasing the brightness of that pixel by a specific amount and multiplying the brightness of a corresponding pixel of the color flow mode image by the increased brightness of the pixel of the B-mode image and, if the brightness of a pixel of the B-mode image is higher than the threshold, image brightness is varied by simply multiplying the brightness of a corresponding pixel of the color flow mode image by the original brightness of the pixel of the B-mode image.

5. An ultrasound diagnostic apparatus which transmits an ultrasonic pulse signal to a specified region of a living body including its moving parts such as a blood flow and displays a status within said region of the living body based on reflected ultrasonic waves which have been received, said ultrasound diagnostic apparatus comprising:

B-mode image display signal acquisition means for acquiring a B-mode image display signal derived from said region;

power Doppler image display signal acquisition means for acquiring a power Doppler image display signal which represents blood flow intensities in colors;

translucent display processing means which performs a translucent display operation on the B-mode image display signal fed from the B-mode image display signal acquisition means and the power Doppler image display signal fed from the power Doppler image display signal acquisition means; and a display means displaying a synthesized image produced by superimposing a B-mode image and a power Doppler image based on a signal fed from the translucent display processing means.

6. An ultrasound diagnostic apparatus according to claim 5 wherein the translucent display operation is accomplished by varying the brightness of each pixel of the power Doppler image in accordance with the brightness of a corresponding pixel of the B-mode image.

7. An ultrasound diagnostic apparatus according to claim 6 wherein image brightness is varied by inverting the brightness of each pixel of the B-mode image and multiplying the inverted brightness by the brightness of a corresponding pixel of the B-mode image.

8. An ultrasound diagnostic apparatus which transmits an ultrasonic pulse signal to a specified region of a living body including its moving parts such as a blood flow and displays a status within said region of the living body based on reflected ultrasonic waves which have been received, said ultrasound diagnostic apparatus comprising:

> B-mode image display signal acquisition means for acquiring a B-mode image display signal derived from said region;
>
> color flow mode image display signal acquisition means for acquiring a color flow mode image display signal representing information on movements of blood and other moving parts in a plurality of colors;
>
> first translucent display processing means which performs a translucent display operation on the B-mode image display signal fed from the B-mode image display signal acquisition means and the color flow mode image display signal fed from the color flow mode image display signal acquisition means;
>
> power Doppler image display signal acquisition means for acquiring a power Doppler image display signal which represents blood flow intensities in colors of a single hue;
>
> second translucent display processing means which performs a translucent display operation on the B-mode image display signal fed from the B-mode image display signal acquisition means and the power Doppler image display signal fed from the power Doppler image display signal acquisition means; and
>
> display means which selectively displays a synthesized image based on a signal fed from the first or second translucent display processing means.

9. An ultrasound diagnostic apparatus according to claim 1, 5 or 8 wherein the information on the movements of blood and other moving parts or blood flow intensities are displayed in colors of a single hue.

10. An ultrasound diagnostic apparatus according to claim 1 or 8 wherein the information on the movements of blood and other moving parts is the variance of the blood flow.

\* \* \* \* \*